(12) United States Patent
Hoshino et al.

(10) Patent No.: US 8,663,697 B2
(45) Date of Patent: Mar. 4, 2014

(54) SOLID DISPERSION PREPARATION

(71) Applicant: Shin-Etsu Chemical Co., Ltd., Tokyo (JP)

(72) Inventors: Takafumi Hoshino, Joetsu (JP); Fumie Kusaki, Joetsu (JP); Ikuo Fukui, Joetsu (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 0 days.

(21) Appl. No.: 13/710,892

(22) Filed: Dec. 11, 2012

(65) Prior Publication Data

US 2013/0172392 A1   Jul. 4, 2013

Related U.S. Application Data

(62) Division of application No. 11/736,834, filed on Apr. 18, 2007, now Pat. No. 8,354,122.

(30) Foreign Application Priority Data

Apr. 20, 2006 (JP) ................................ 2006-116272
Mar. 29, 2007 (JP) ................................ 2007-087957

(51) Int. Cl.
   *A61K 9/14* (2006.01)
(52) U.S. Cl.
   USPC ........................................................ 424/489
(58) Field of Classification Search
   None
   See application file for complete search history.

(56) References Cited

U.S. PATENT DOCUMENTS

| | | | | |
|---|---|---|---|---|
| 4,888,177 | A * | 12/1989 | Gergely et al. | ............... 424/466 |
| 5,340,591 | A | 8/1994 | Nakano et al. | |
| 6,046,177 | A | 4/2000 | Stella et al. | |
| 6,379,707 | B2 | 4/2002 | Vladyka, Jr. et al. | |
| 6,497,905 | B1 | 12/2002 | Vladyka, Jr. et al. | |
| 6,511,681 | B2 | 1/2003 | Vladyka, Jr. et al. | |
| 6,559,134 | B2 | 5/2003 | Tanno et al. | |
| 2003/0224043 | A1 | 12/2003 | Appel et al. | |
| 2004/0057993 | A1 | 3/2004 | Jain et al. | |
| 2005/0003001 | A1 | 1/2005 | Yamaguchi et al. | |
| 2005/0009806 | A1 | 1/2005 | Patel et al. | |
| 2005/0095289 | A1 | 5/2005 | Takagi et al. | |
| 2005/0158386 | A1 | 7/2005 | Tanno et al. | |

FOREIGN PATENT DOCUMENTS

| | | |
|---|---|---|
| EP | 0 957 112 A2 | 11/1999 |
| EP | 1 064 942 A1 | 1/2001 |
| EP | 1 133 984 A1 | 9/2001 |
| JP | 5-262642 A | 10/1993 |
| JP | 07-118154 A | 5/1995 |
| JP | 2000-154137 A | 6/2000 |
| JP | 2001-114703 A | 4/2001 |
| JP | 2004-67606 A | 3/2004 |
| JP | 2005-517690 A | 6/2005 |
| WO | 00/56726 A1 | 9/2000 |
| WO | 03/068266 A1 | 8/2003 |
| WO | 2005/046696 A1 | 5/2005 |
| WO | 2005/079748 A2 | 9/2005 |

OTHER PUBLICATIONS

Noriyuki Hirasawa et al., Stability of Nilvadipine Solid Dispersion Tablet With Non-Packaging Condition; Yakugaku Zasshi, vol. 124(1), pp. 19-23, 2004 The Pharmaceutical Society of Japan; Partial English Translation, p. 19, Right Column, Line 16 to p. 20, Left Column, Line 27.

Japanese Office Action Mail Date Feb. 8, 2013 and English Translation in Corresponding Japanese Patent Application No. 2007-087957.

Yakugyo Jiho Sha, Design and Evaluation of Oral Administration Prepareations, Partial English Translation, Feb. 10, 1995, pp. 172-179, Translation of p. 176, Lines 7-12 and Fig. 7-6.

* cited by examiner

*Primary Examiner* — Paul Dickinson
(74) *Attorney, Agent, or Firm* — Roberts Mlotkowski; Safran & Cole, P.C.; David S. Safran

(57) ABSTRACT

A granule or a tablet of a solid dispersion that allows a drug in a preparation to be rapidly dissolved without impairing dissolving of the solid dispersion, and a method for producing same is composed of 1 to 10% by weight of a poorly soluble drug, a water-soluble polymer, an excipient and 15 to 50% by weight if a disintegrator; a tablet of a solid dispersion composed of a poorly soluble drug, 1 to 5% by weight of a water-soluble polymer, an excipient and 15 to 50% by weight of a disintegrator; and a method for producing a granule or tablet of a solid dispersion comprising spraying a water-soluble polymer solution, in which a poorly soluble drug has been dispersed or dissolved, on a mixed powder of an excipient and a disintegrator, and granulating and drying a resultant.

2 Claims, No Drawings

SOLID DISPERSION PREPARATION

CROSS REFERENCE TO RELATED APPLICATION

This application is a division of commonly owned, co-pending U.S. patent application Ser. No. 11/736,834, filed Apr. 18, 2007.

BACKGROUND OF THE INVENTION

1. Field of the Invention

The present invention relates to a solid preparation produced for improving the dissolution of a poorly soluble drug, particularly to a solid preparation comprising a solid dispersion that can be rapidly disintegrated and that allows a drug to be dissolved.

2. Description of the Related Art

Poorly soluble drugs have high crystallinity and extremely low solubility in water. Thus, bioavailability or internal absorption of preparations produced from these drugs is low so that there is a problem in that the drug action is insufficient. As a technique for addressing this problem, a solid dispersion has been developed in which molecules of a poorly soluble drug are dispersed in a polymer carrier such as a cellulose derivative, in an amorphous state.

Conventional solid dispersions are used as preparations in the form of capsules containing a solid obtained by spray-drying a cosolvent in which a poorly soluble drug and a carrier are dissolved, or in the form of fine granules or granules as they are. The form of tablets, which is a generally used dosage form of solid preparations, is most preferable because tablets are easily prescribed and administered in a fixed dose, and easily handled and taken by patients.

It is known that in the case of tablets produced from a solid dispersion powder, the porosity of the tablets is often lowered not only due to a reduced specific surface area, but also due to plastic deformation of amorphous drug molecules during a compression-molding process and strong bonding between carrier polymers. This low porosity leads to slow permeation of water molecules into the tablets in administration, and to slow disintegration of the tablets, and thus the solid dispersion cannot exert its original effect of improving the dissolution. Furthermore, the viscosity of a water-soluble or enteric polymer serving as a carrier increases during hydration or dissolution, and thus a type of hydrogel layer is formed on the surface of the tablets during dissolution, so that water is further prevented from infiltrating.

As means for addressing these problems, Japanese Patent Application (PCT National Phase) Unexamined Publication No. 2005-517690 has proposed a tablet comprising a solid dispersion powder, a disintegrator and an excipient comprising porosigen, and obtained by spray-drying. Furthermore, Japanese Patent Application Unexamined Publication No. 5-262642/1993 has proposed a powder in which a water-soluble polymer base and if necessary, an excipient and a disintegrator are added to a poorly soluble drug. However, an added amount of a concentration-enhancing polymer or a water-soluble polymer base, serving as carriers, is large, and thus the rate at which a drug is dissolved tends to be lowered. Furthermore, in the case of a solid dispersion powder obtained by spray-drying as in Japanese Patent Application (PCT National Phase) Unexamined Publication No. 2005-517690, it is necessary that after the solid dispersion powder is mixed with the other ingredients, the mixture is compressed and pulverized for formation of a granulated powder for tableting. The particle size of the solid dispersion powder prepared by spray-drying in this manner is small, and thus when it is simply mixed with an excipient, segregation is caused so that ingredients are not distributed uniformly in the powder for tableting. Moreover, this process makes the operation complicated, and the solid dispersion may be recrystallized in compression. Furthermore, the disintegrator is added after the solid dispersion has been prepared, and thus when the solid dispersion is aggregated and bonded in the tablet due to high bonding strength of the carrier, aggregation may be formed and dispersed in water during disintegration, lowering the dissolution of the drug.

Japanese Patent Application Unexamined Publication No. 2004-67606 has proposed a tablet comprising fine granules obtained by spraying a solution containing itraconazole, which is a poorly soluble drug, a water-soluble polymer and an enteric polymer, on a mixed powder of an excipient and a disintegrator, granulating and drying the resultant. However, the amount of the disintegrator added is small and it takes as long as 360 minutes for the drug to be dissolved from the tablet. Thus, the disintegratability of the tablet is not improved.

Hirasawa et al. (Journal of the Pharmaceutical Society of Japan, 124(1), 19-23 (2004)) has proposed a tablet produced by loading an ethanol dispersion as a binding liquid containing nilvadipine which is a poorly soluble drug, crospovidone and methylcellulose, into a mixed powder of materials such as lactose, methylcellulose and low-substituted hydroxypropylcellulose, and agitating and granulating the mixture. The nilvadipine is soluble in ethanol, but crospovidone and methylcellulose are not soluble in ethanol. Thus, it seems that the ethanol functions only as an agent for dispersing and diluting amorphous nilvadipine because a co-dissolved state is not obtained. In order to disperse amorphous drug molecules in a polymer serving as a carrier, it is necessary to obtain a co-dissolved state in a cosolvent in which both the drug molecules and the polymer are dissolved. Thus, it seems that the solid dispersion of amorphous nilvadipine described in Journal of the Pharmaceutical Society of Japan 124(1), 19-23 (2004) does not have sufficient solubility. Furthermore, since an amount of water-soluble polymer added is large, it may be difficult to obtain a preparation that can be rapidly dissolved.

SUMMARY OF THE INVENTION

The present invention was reached in view of the above-described circumstances, and it is an object thereof to provide a granule or a tablet of a solid dispersion that allows a drug in a preparation to be rapidly dissolved without impairing the dissolution of the solid dispersion, and a method for producing the same.

The inventors had conducted an in-depth study in order to address the above-described problem, and found that when a water-soluble polymer serving as a carrier of a solid dispersion and a disintegrator are added in predetermined amounts, respectively, disintegratability is not lowered in tablets obtained by compression-molding the solid dispersion, and granules and tablets have excellent solubility. Thus, the present invention has been achieved.

More specifically, the present invention provides a granule of a solid dispersion comprising a poorly soluble drug, a water-soluble polymer, an excipient and a disintegrator, wherein a content of the water-soluble polymer is 1 to 10% by weight and a content of the disintegrator is 15 to 50% by weight; a tablet of a solid dispersion comprising a poorly soluble drug, a water-soluble polymer, an excipient and a disintegrator, wherein a content of the water-soluble polymer is 1 to 5% by weight and a content of the disintegrator is 15 to 50% by weight; and a method for producing a granule or tablet of a solid dispersion comprising spraying a water-soluble polymer solution in which a poorly soluble drug has been dispersed or dissolved, on a mixed powder of an excipient and a disintegrator, and granulating and drying the resultant.

According to the present invention, a solid preparation with excellent solubility is obtained that has high solubility in the case of a granule, and that can be disintegrated and release at least 70% by weight of a poorly soluble drug within 10 minutes after the introduction to a dissolution medium in the case of a tablet.

DETAILED DESCRIPTION OF THE PREFERRED EMBODIMENTS

Hereinafter, the present invention is described in more detail.

A poorly soluble drug used in the present invention has extremely low solubility in water, and poor absorption in ordinary oral administration. For example, the poorly soluble drug means a drug that is "practically insoluble or insoluble" or "very slightly soluble" as prescribed in the Japanese Pharmacopoeia Fourteenth Edition. The term "solubility" of a drug in the Japanese Pharmacopoeia Fourteenth Edition means the degree of dissolution of the drug, powdered in the case of a solid, within 30 minutes in a solvent at 20±5° C., by shaking for 30 seconds each time at 5-minute intervals. If a drug is "practically insoluble or insoluble", then an amount of solvent (water, in this specification) required for dissolving 1 g or 1 ml of the drug is 10,000 ml or more. If a drug is "very slightly soluble", then an amount of solvent required for dissolving 1 g or 1 ml of the drug is 1,000 ml or more and less than 10,000 ml.

Specific examples of the poorly soluble drug used in the present invention may include, but are not limited to, nifedipine, phenacetin, phenyloin, digitoxin, nilvadipine, diazepam, griseofulvin and chloramphenicol.

In the present invention, since molecules of a poorly soluble drug are dispersed in an amorphous state, a water-soluble polymer is used as a carrier. The water-soluble polymer is a polymer that is "very soluble (an amount of water required for dissolving 1 g or 1 ml of the drug is less than 1 ml)", "freely soluble (an amount of water required for dissolving 1 g or 1 ml of the drug is 1 ml or more and less than 10 ml)", or "soluble (an amount of water required for dissolving 1 g or 1 ml of the drug is 10 ml or more and less than 30 ml)" as prescribed in the Japanese Pharmacopoeia Fourteenth Edition, when the polymer is added to hot water (70° C. or higher) ranging from half to the total amount required for dissolution and the mixture is agitated and dispersed, while in a case that the amount of hot water used is less than the total amount required cold water or ice water in the remaining amount is added with agitation. Specific examples thereof may include alkylcellulose such as methylcellulose; hydroxyalkylcellulose such as hydroxyethylcellulose and hydroxypropylcellulose; hydroxyalkylalkylcellulose such as hydroxyethylmethylcellulose and hydroxypropylmethylcellulose; polyvinyl alcohol; and polyvinyl pyrrolidone. Of these, hydroxypropylmethylcellulose may be particularly preferable.

The content of the water-soluble polymer may vary depending on the dosage form of the solid preparation. If the solid preparation is in the form of granule, then the preferable content may be 1 to 10% by weight with respect to the total amount of the preparation. If the solid preparation is in the form of tablet, then the preferable content may be 1 to 5% by weight with respect to the preparation. If the content of the water-soluble polymer is less than 1% by weight, then it may be difficult to obtain a completely amorphous state of the poorly soluble drug in a solid dispersion. If the content is more than 10% by weight in the case of granule, or more than 5% by weight in the case of tablet, then the portion of the water-soluble polymer in the preparation becomes large, which is not preferable because the dosage amount of the granule or the size of the tablet may become large.

The weight ratio of the water-soluble polymer to the poorly soluble drug may be preferably 1 to 5 when taking the poorly soluble drug as 1. If the ratio of the water-soluble polymer is less than 1, then the poorly soluble drug in the solid dispersion may not be in a completely amorphous state. If the ratio is more than 5, then the ratio of the water-soluble polymer in the preparation becomes large, and thus the size of the preparation becomes large, which may not be suitable for a generally used preparation.

The solvent for preparing the solid dispersion comprising the water-soluble polymer and the poorly soluble drug may be preferably a solvent in which the poorly soluble drug is well dissolved and the water-soluble polymer is also dissolved. Examples of the solvent may include methanol, ethanol, methylene chloride, acetone, a mixture thereof and their mixed solvents with water. The solvent may be selected appropriately based on the solubility of the poorly soluble drug and the water-soluble polymer in the solvent.

The solvent may be added in an amount at which the solid concentration is preferably 3 to 18% by weight, particularly preferably 3.5 to 12% by weight.

Examples of the excipient used in the present invention may include lactose, cornstarch, saccharose, mannite, anhydrous calcium phosphate, crystalline cellulose and their mixtures. It may be particularly preferable to use a mixed powder comprising lactose and cornstarch in a weight ratio of 7:3.

The content of the excipient may be preferably 30 to 90% by weight, particularly preferably 42.5 to 78.5% by weight, with respect to the total amount of the preparation. If the content of the excipient is less than 30% by weight, then the amount of the disintegrator may become too large and thus the flowability of the granulated powder may be poor. If the content is more than 90% by weight, then the amount of the disintegrator becomes small, and thus an effect of improving solubility may not be expected.

Examples of the disintegrator used in the present invention may include carmellose, carmellose sodium, carmellose calcium, croscarmellose sodium, low-substituted hydroxypropylcellulose (L-HPC) having 5 to 16% by weight of hydroxypropoxyl groups, hydroxypropyl starch, sodium carboxymethyl starch, crospovidone and their mixtures.

As the disintegrator used in the present invention, low-substituted hydroxypropylcellulose may be particularly preferable because it provides granulates with high flowability and ensures high dissolution from the compression-molded preparation. The low-substituted hydroxypropylcellulose having a loose bulk density of 0.40 g/ml or more and a tapped bulk density of 0.60 g/ml or more may be particularly preferable.

Herein, the term "loose bulk density" means the bulk density in a loosely filled state and is measured by uniformly supplying a sample from 23 cm above, through a sieve with 24 mesh of Japanese Industrial Standards (JIS), to a cylindrical vessel of stainless steel having a diameter of 5.03 cm and a height 5.03 cm (volume 100 ml), and performing weighing after leveling at the upper surface. The term "tapped bulk density" means the bulk density in a tightly filled state obtained by performing tapping on the vessel in the loosely filled state. The tapping means an operation to make the sample be tightly filled, by repeatedly dropping the vessel filled with the sample from a predetermined height thereby providing the bottom portion with a light impact. In practice, when weighing has been completed after leveling at the upper surface in the measurement of the loose bulk density, a cap (a component of a powder tester manufactured by Hosokawa Micron Corporation) is placed on the vessel, powder is added to the upper edge of the cap, and tapping is performed 180 times at a tapping height of 1.8 cm. When the tapping has been completed, the cap is removed and weighing is performed after leveling the powder at the upper surface of the vessel. The bulk density in this state is taken as the tapped bulk density. These operations can be performed using a powder tester (PT-D) manufactured by Hosokawa Micron Corporation.

Furthermore, the low-substituted hydroxypropylcellulose having a degree of compression of 35% or less may be preferable. Herein, the degree of compression means the degree of volume decreased and is obtained by the following equation:

Degree of compression (%)={(tapped b.d.−loose b.d.)/ tapped b.d.}×100 wherein b.d. means bulk density.

The content of the disintegrator may be preferably 15 to 50% by weight, particularly preferably 20 to 40% by weight, with respect to the total amount of the preparation. If the content of the disintegrator is less than 15% by weight, then an effect of improving solubility may be weak and an expected effect may not be obtained. If the content is more than 50% by weight, then the flowability of the obtained granule powder may be lowered, which is not preferable for powder for tableting.

If necessary, a lubricant may be added to the tablet of the solid dispersion of the present invention. Examples of the lubricant may include magnesium stearate, sucrose fatty acid ester, polyethylene glycol, talc and stearic acid.

The amount of the lubricant may be preferably 0.5 to 2% by weight with respect to the amount of the preparation excluding the lubricant. If the amount of the lubricant added is less than 0.5% by weight, then sufficient lubricative properties may not be obtained so that the preparation may adhere to a mortar or a pestle during tableting. If the amount is more than 2% by weight, then hardness or disintegratability may be lowered.

Next, methods for producing granules and tablets of the solid dispersion of the present invention will be described.

The granule of the solid dispersion of the present invention can be obtained by spraying a water-soluble polymer solution in which the poorly soluble drug has been dispersed or dissolved, on a mixed powder of the excipient and the disintegrator, and granulating and drying the resultant. More specifically, the water-soluble polymer solution in which the poorly soluble drug has been dispersed or dissolved is sprayed on the mixed powder of the excipient and the disintegrator which is flowing in a granulator, the resultant is granulated and dried, and then the particle size regulation is carried out.

Examples of the granulator may include a fluidized bed granulation coating device, a high speed agitation granulating device and a rolling granulating device. The fluidized bed granulation coating device may be particularly preferable.

Using the granules obtained by the above-described method as powder for tableting, the tablets of the present invention may be obtained by adding an optional lubricant to the granules and compression-molding the granules in a tableting machine. The granules obtained by the above-described method may be also pulverized by using an appropriate pulverizer before the tableting when the pulverization is needed for powder properties, improvement of dissolution or the like. The pulverizer may include a knife mill, a roller mill, a ball mill, a jet mill, a screening mil and a beads mill.

When the thus obtained granules of the solid dispersion are evaluated following "Dissolution Test, Method 2" described in the Japanese Pharmacopoeia Fourteenth Edition, the concentration of the drug dissolved within 5 minutes after administration may be 70% or more with respect to the dose. Thus, high dissolution is exhibited.

When the obtained tablets of the solid dispersion are evaluated following "Disintegration Test" described in the Japanese Pharmacopoeia Fourteenth Edition, the tablets may be disintegrated within 10 minutes after administration, and when the tablets are evaluated following "Dissolution Test, Method 2" described in the Japanese Pharmacopoeia Fourteenth Edition, the concentration of the drug dissolved within 10 minutes after administration may be 70% or more with respect to the dose. Thus, high disintegratability and high dissolution are exhibited.

The solid preparation obtained in the present invention may be coated by known methods in order to provide taste-masking or odor-masking, to make the preparation enteric, or to achieve sustained release of the preparation. Examples of the coating agent may include enteric polymers such as cellulose acetate phthalate, methacrylic acid copolymer L, methacrylic acid copolymer LD, methacrylic acid copolymer S, hydroxypropylmethylcellulose phthalate, hydroxypropylmethylcellulose acetate succinate and carboxymethylethylcellulose; polymers soluble in stomach such as polyvinyl acetal diethylaminoacetate and aminoalkyl methacrylate copolymer; and the water-soluble polymers described above.

Hereinafter, the present invention will be specifically described by way of examples and comparative examples, but it should not be construed that the present invention is limited to these examples.

Example 1 and Comparative Example 1

A solid dispersion solution was prepared by dissolving 1.2 g of nifedipine and 2.4 g of hydroxypropylmethylcellulose (HPMC) (8.7% by weight of hydroxypropoxyl groups and 28.8% by weight of methoxyl groups, 6 mPa·s), or 12 g of nifedipine and 24 g of hydroxypropylmethylcellulose (HPMC) (8.7% by weight of hydroxypropyl groups and 28.8% by weight of methoxyl groups, 6 mPa·s), in a mixed solvent containing ethanol and water in a weight ratio of 8:2. The solid dispersion solution was sprayed on the mixture of low-substituted hydroxypropylcellulose (L-HPC) (10.9% by weight of hydroxypropoxyl groups), lactose (Pharmatose manufactured by DMV International) and cornstarch (cornstarch W manufactured by Nihon Shokuhin Kako Co., Ltd.) which had been flowing in a fluidized bed granulation coating device (Multiplex MP-01 manufactured by POWREX CORPORATION), and the resultant was granulated and dried. Then the particle size was regulated with a sieve of 30 mesh (opening: 500 μm) to yield granules. As a comparative example, granules containing as a disintegrator the low-substituted hydroxypropylcellulose with the amounts outside of the range specified by the present invention were produced in a similar manner.

Table 1 shows results of the flowability evaluation when 20 g each of the obtained granules having various formulae was evaluated using the orifice flowability index. Herein, the orifice flowability index means the index for evaluating the flowability of powder and is obtained by placing 20 g of sample in an hourglass-shaped funnel (inner diameter: 42 mm, height: 90 mm) with its orifice blocked, allowing the sample to flow down through the orifice, and evaluating the flowability based on the orifice size.

The evaluation "good" for flowability means good flowablity and rapid flow-down of the powder, while the evaluation "poor" means poor flowability and the powder did not flow down through the orifice.

TABLE 1

| | | composition | | | | | | |
|---|---|---|---|---|---|---|---|---|
| | | nifedipine (g) | HPMC (g) | L-HPC (g) | lactose (g) | cornstarch (g) | total (g) | flowability |
| Example 1 | formula A | 1.2 | 2.4 | 48 | 131.9 | 56.5 | 240 | good |
| | formula B | 12 | 24 | 48 | 109.2 | 46.8 | 240 | good |
| | formula C | 12 | 24 | 96 | 75.6 | 32.4 | 240 | good |
| Comp. Ex. 1 | formula D | 12 | 24 | — | 142.8 | 61.2 | 240 | good |
| | formula E | 12 | 24 | 24 | 126 | 54 | 240 | good |
| | formula F | 12 | 24 | 144 | 42 | 18 | 240 | poor |

Example 2 and Comparative Example 2

Among the granules obtained in Example 1 and Comparative Example 1, 1890 mg of granules (containing 94.5 mg of nifedipine) with good flowability were tested in accordance with the Paddle method of the Dissolution Test in the Japanese Pharmacopoeia Fourteenth Edition. As the conditions for the Dissolution Test, the rotational speed was set to 100 rpm, and 900 ml of water was used as a test fluid. For the sake of reference, 94.5 mg of nifedipine powder alone was also tested in a similar manner. Table 2 shows the results.

All of the granules (Formulae A to C) of Example 2 exhibited dissolution higher than that of the granules of Comparative Example 2. On the other hand, Formula E in which the amount of the low-substituted hydroxypropylcellulose serving as the disintegrator was smaller than the range specified by the present invention, exhibited the similar vales to those obtained for Formula D in which the low-substituted hydroxypropylcellulose was not added, and thus the solubility was not substantially improved. Formula F in which the amount of the low-substituted hydroxypropylcellulose was large, blocking was caused during fluidized bed granulation and thus it was difficult to perform good granulation.

As a result, it is evident that the granules of the solid dispersion of the present invention have excellent solubility.

Example 3 and Comparative Example 3

A solid dispersion solution was prepared by dissolving 1.2 g of nifedipine and 2.4 g of hydroxypropylmethylcellulose (HPMC) (8.7% by weight of hydroxypropoxyl groups and 28.8% by weight of methoxyl groups), or 6 g of nifedipine and 12 g of hydroxypropylmethylcellulose (HPMC) (8.7% by weight of hydroxypropyl groups and 28.8% by weight of methoxyl groups), in a mixed solvent containing ethanol and water in a weight ratio of 8:2. The solid dispersion solution was sprayed on a mixture of low-substituted hydroxypropylcellulose (L-HPC) (10.9% by weight of hydroxypropoxyl groups), lactose (Pharmatose manufactured by DMV International) and cornstarch (cornstarch W manufactured by Nihon Shokuhin Kako Co., Ltd.) which had been flowing in a fluidized bed granulation coating device (Multiplex MP-01 manufactured by POWREX CORPORATION). The resultant was granulated and dried, and the particle size was regulated with a sieve of 30 mesh (opening: 500 μm). Thus, granules were obtained. Using the granules as powder for tableting, 0.5% by weight of magnesium stearate as a lubricant was added to the powder for tableting, mixing the resultant, and processing the mixture in a rotary tableting machine (Vergo manufactured by Kikusui Seisakusho Ltd.). As a result, 210 mg of tablets were produced. As a comparative example, tablets containing as a water-soluble polymer the hydroxypropylmethylcellulose with amounts outside of the range specified by the present invention were produced in similar manner. The obtained tablets were tested in terms of hardness and disintegratability. The results are shown in Table 3.

The tablets (Formulae G to I) obtained in Example 3 exhibited appropriate hardness and excellent disintegratability.

On the other hand, the tablets (Formulae J to L) obtained in Comparative Example 3 containing as a water-soluble poly-

TABLE 2

| | | dissolution (%) time (minunites) | | | | | | | | |
|---|---|---|---|---|---|---|---|---|---|---|
| | | 0 | 2 | 5 | 10 | 15 | 20 | 30 | 45 | 60 |
| Ex. 2 | formula A | 0 | 67.4 | 71.6 | 70.6 | 68.3 | 67.3 | 65.2 | 62.9 | 62.0 |
| | formula B | 0 | 53.7 | 71.3 | 69.7 | 66.7 | 65.9 | 61.8 | 60.8 | 59.5 |
| | formula C | 0 | 65.8 | 73.1 | 70.4 | 68.3 | 67.7 | 65.9 | 64.0 | 61.6 |
| Comp. Ex. 2 | formula D | 0 | 46.9 | 59.8 | 61.2 | 59.8 | 58.2 | 57.0 | 54.9 | 54.1 |
| | formula E | 0 | 56.5 | 58.2 | 60.2 | 59.0 | 57.4 | 55.3 | 54.1 | 52.3 |
| | formula F | — | — | — | — | — | — | — | — | — |
| | nifedipine alone | 0 | 0.6 | 3.4 | 9.3 | 10 | 10.6 | 11.9 | 11.9 | 11.9 | mer the hydroxypropylmethylcellulose with amounts outside of the range specified by the present invention exhibited the lowered disintegratability.

Thus, it is evident that the tablets of the solid dispersion of the present invention have excellent disintegratability and excellent solubility.

TABLE 3

| | | composition | | | | | | | |
|---|---|---|---|---|---|---|---|---|---|
| | | nifedipine (g) | HPMC (g) | L-HPC (g) | lactose (g) | cornstarch (g) | total (g) | hardness (kgf) | distintegration time (minutes) |
| Example 3 | formula G | 1.2 | 2.4 | 48 | 131.9 | 56.5 | 240 | 7 | 4.3 |
| | formula H | 6 | 12 | 48 | 121.8 | 52.2 | 240 | 7.4 | 7.4 |
| | formula I | 6 | 12 | 96 | 88.2 | 37.8 | 240 | 6.1 | 7.1 |
| Comp. Ex. 3 | formula J | 6 | 12 | — | 155.4 | 66.6 | 240 | 10 | 24.4 |
| | formula K | 12 | 24 | 48 | 109.2 | 46.8 | 240 | 10 | 21.6 |
| | formula L | 12 | 24 | 96 | 75.6 | 32.4 | 240 | 9.4 | 25.3 |

Example 4 and Comparative Example 4

The Dissolution Test was conducted on 1890 mg of the tablets (containing 47.25 mg of nifedipine) obtained in Example 3 and Comparative Example 3 in the same manner as in Example 2. Furthermore, for the sake of reference, 47.25 mg of nifedipine powder alone was also tested in a similar manner. The results are shown in Table 4.

The tablets (Formulae G to I) obtained in Example 4 exhibited dissolution results that were by no means inferior to that of the granulated powder. Furthermore, the dissolution was improved by increasing the amount of the disintegrator. The solubility was not substantially improved for Formula J in which the low-substituted hydroxypropylcellulose serving as the disintegrator was not added.

On the other hand, for Formulae J and K containing as a water-soluble polymer the hydroxypropylmethylcellulose with the amount outside of the range specified by the present invention, hydrogel of the water-soluble polymer was formed on the surface of the tablets during the test and thus sustained release of letting dissolution start from the surface as time passed took place, so that extended disintegration time and insufficient improvement of dissolution were observed as in conventional examples.

TABLE 4

| | | dissolution (%) time (minutes) | | | | | | | | |
|---|---|---|---|---|---|---|---|---|---|---|
| | | 0 | 2 | 5 | 10 | 15 | 20 | 30 | 45 | 60 |
| Example 4 | formula G | 0 | 42.0 | 74.6 | 83.9 | 79.3 | 76.9 | 70.7 | 71.5 | 70.7 |
| | formula H | 0 | 41.4 | 66.3 | 71.2 | 72.1 | 63.8 | 65.4 | 67.1 | 63.0 |
| | formula I | 0 | 39.8 | 69.6 | 81.2 | 79.5 | 77.9 | 77.0 | 78.7 | 84.5 |
| Comp. Ex. 4 | formula J | 0 | 7.5 | 21.8 | 42.8 | 50.3 | 49.5 | 52.8 | 51.1 | 50.3 |
| | formula K | 0 | 7.6 | 17.1 | 25.4 | 31.2 | 33.1 | 35.0 | 35.9 | 36.6 |
| | formula L | 0 | 9.2 | 17.8 | 25.9 | 30.4 | 33.2 | 35.4 | 39.9 | 39.1 |
| nifedipine alone | | 0 | 0.6 | 3.4 | 9.3 | 10 | 10.6 | 11.9 | 11.9 | 11.9 |

The invention claimed is:

1. A granule of a solid dispersion comprising a poorly water-soluble drug, a water-soluble polymer, an excipient and a disintegrator, wherein a content of the water-soluble polymer is 1 to 10% by weight and a content of the disintegrator is 15 to 50% by weight; the water-soluble polymer is selected from the group consisting of alkylcellulose, hydroxyalkylcellulose, hydroxyalkylalkylcellulose, polyvinyl alcohol and polyvinyl pyrrolidone; the disintegrator is low-substituted hydroxypropylcellulose having 5 to 16% by weight of hydroxypropoxyl groups; and molecules of the poorly water-soluble drug in an amorphous state are dispersed in the water-soluble polymer as a result of dissolution of the poorly water-soluble drug and the water-soluble polymer in a solvent.

2. The granule of the solid dispersion according to claim 1, wherein the disintegrator is low-substituted hydroxypropylcellulose having a loose bulk density of at least 0.40 g/ml and a tapped bulk density of at least 0.60 g/ml.

* * * * *